United States Patent [19]

Imai

[11] 4,250,115

[45] Feb. 10, 1981

[54] PREPARATION OF TERTIARY AMINES

[75] Inventor: Tamotsu Imai, Mt. Prospect, Ill.

[73] Assignee: UOP Inc., Des Plaines, Ill.

[21] Appl. No.: 971,282

[22] Filed: Dec. 20, 1978

[51] Int. Cl.$^3$ .............................................. C07C 85/18
[52] U.S. Cl. .................. 564/436; 252/429 R; 252/441; 252/443; 252/472; 564/433; 564/467
[58] Field of Search ................ 260/563 R, 576, 577, 260/583 R, 585 D, 570.8, 570.9

[56] References Cited

U.S. PATENT DOCUMENTS

| | | | |
|---|---|---|---|
| 2,422,632 | 6/1947 | Olin et al. | 260/563 R X |
| 2,497,310 | 2/1950 | Larson | 260/585 |
| 3,513,200 | 5/1970 | Biale | 260/583 |
| 3,574,717 | 4/1971 | Lloyd | 260/585 D X |
| 3,758,586 | 9/1973 | Coulson | 260/583 R |
| 4,096,150 | 6/1978 | Berthoux et al. | 260/576 X |

*Primary Examiner*—John Doll
*Attorney, Agent, or Firm*—James R. Hoatson, Jr.; Raymond H. Nelson; William H. Page, II

[57] ABSTRACT

Tertiary amines may be prepared by reacting an olefinic compound, carbon monoxide, hydrogen and a nitrogen-containing compound such as ammonia, a primary amine or a secondary amine in the presence of a rhodium or ruthenium-containing catalyst at temperatures in the range of from about 50° to about 350° C. and a pressure in the range of from about 10 to about 300 atmospheres.

10 Claims, No Drawings

PREPARATION OF TERTIARY AMINES

BACKGROUND OF THE INVENTION

Heretofore tertiary amines have been prepared in a wide variety of reactions utilizing various metal-containing compounds as catalysts. For example, U.S. Pat. No. 3,091,641 discloses a process for preparing tertiary amines in which a secondary amine and an aliphatic ketone are reacted with carbon monoxide and water in the presence of an iron carbonyl catalyst such as iron pentacarbonyl or biscyclopentadienyl diiron tetracarbonyl. Another U.S. patent, namely, U.S. Pat. No. 2,497,310 discloses the synthesis of amines in which an unsaturated compound, carbon monoxide, hydrogen and ammonia or a substitute ammonia are reacted in the presence of a cobalt catalyst although other catalysts which possess hydrogenation properties such as nickel, ruthenium, iron and copper may also be used. Another prior art reference, namly, U.S. Pat. No. 3,947,458 is drawn to a process for preparing amines in which nitrogen-containing compounds and an olefin along with carbon monoxide and water are reacted in the presence of a catalyst comprising iron pentacarbonyl and a rhodium compound. In like manner, U.S. Pat. No. 3,234,283 also discloses a process for the preparation of trialkyl amines in which an olefin is reacted with carbon monoxide, hydrogen and a dialkyl amine in the presence of a catalyst consisting essentially of cobalt carbonyl trihydrocarbonphosphene. The hydrocarbon content of the catalyst is limited to trihydrocarbons containing a total of up to about 30 carbon atoms, the number of carbon atoms in any one of said hydrocarbon radicals not exceeding 18. Other prior art patents include U.S. Pat. No. 3,758,586 in which ethylene is reacted with secondary aliphatic amines in the presence of rhodium or iridium catalysts to form a tertiary amine in which one of the substituents is, of necessity, ethylene; U.S. Pat. No. 3,513,200 in which the preparation of tertiary amines is accomplished by reacting a secondary amine containing from 2 to about 20 carbon atoms with an aliphatic hydrocarbon olefin containing from about 2 to about 20 carbon atoms, as well as carbon monoxide and hydrogen in the presence of a complex catalyst comprising a Group VIII noble metal hydride in complex with a biphyllic ligand, said ligand containing phosphoric, arsenic or antimony; U.S. Pat. No. 3,412,158 which is drawn to a process for the preparation of aliphatic amines from the reaction of lower molecular weight olefins and ammonia, the primary product comprising a primary amine rather than a tertiary amine; U.S. Pat. No. 2,501,509 which is drawn to the preparation of amines by heating an ammonia type compound with a hydrocarbon olefinic compound utilizing an alkali metal catalyst such as sodium, this reference requires the presence of an organic liquid diluent for the olefinic reactant; and U.S. Pat. No. 2,422,631 in which aliphatic amines are produced by reacting an olefin, an oxide of carbon, hydrogen and an aminating agent in the presence of a hydrogenation-dehydration catalyst, examples of these catalysts being zinc chromate, zinc tungstate, chromium phosphate, cobalt oxide, iron oxide, etc.

In contradistinction to the above reactions, it will be hereinafter shown in greater detail that tertiary amines may be synthesized by utilizing a particular rhodium or ruthenium-containing catalyst to obtain an economically attractive conversion of the olefin compound with an economically attractive selectivity to the desired product.

This invention relates to a process for the synthesis of tertiary amines. More specifically, the invention is concerned with a process for synthesizing tertiary amines by reacting an olefinic compound with a nitrogen-containing compound, carbon monoxide and hydrogen in the presence of certain catalytic compositions of matter to obtain the desired product.

Tertiary amines will find a wide variety of uses in the chemical field. For example, these compounds may be used in agricultural applications, acting as an inert surfactant for herbicides; for use in corrosion inhibition and crude oil pipelines; in cosmetic formulation; leather processing; paint formulation; secondary oil recovery, mineral separation (cationic flocculation or flotation), etc. A specific compound, namely, tributylamine is used as a solvent, as an intermediate in the preparation of other chemicals and as an inhibitor in hydraulic fluids. In view of these important chemical uses, it is therefore necessary to effect the preparation of the tertiary amines in an economically feasible manner, said process requiring a relatively quantitative conversion of the olefins which are used in the process as well as requiring a high percentage of selectivity to the desired compound. These objectives may be attained by utilizing the process of the present invention in which the reaction is effected in the presence of certain catalytic compositions of matter of the type hereinafter set forth in greater detail.

It is therefore an object of this invention to provide a process for the synthesis of tertiary amines.

A further object of this invention is to provide a process for the synthesis of tertiary amines whereby economical, attractive yields of the desired product are obtained.

In one aspect an embodiment of this invention reisdes in a process for the preparation of tertiary amines which comprises reacting an olefinic compound, carbon monoxide, hydrogen and a nitrogen-containing compound having the formula:

in which the R's are independently selected from the group consisting of hydrogen, alkyl, aryl, cycloalkyl, aralkyl and alkaryl radicals in the presence of a rhodium- or ruthenium-containing catalyst at reaction conditions, and recovering the resultant tertiary amine.

A specific embodiment of this invention is found in a process for the preparation of tertiary amines which comprises reacting undecene, carbon monoxide, hydrogen and dimethylamine at a temperature in the range of from about 50° to about 350° C. and a pressure in the range of from about 10 to about 300 atmospheres in the presence of a catalyst comprising rhodium chloride, and recovering the resultant dodecyldimethylamine.

Other objects and embodiments will be found in the following further detailed description of the present invention.

As hereinbefore set forth, the present invention is concerned with a process for the synthesis of tertiary amines. The desired compounds are prepared by reacting an olefinic compound, a nitrogen-containing compound, carbon monoxide and hydrogen in the presence of certain catalytic compositions of matter and in the absence of added water. The reaction conditions which are employed to produce the desired results will include temperatures in the range of from about 50° to about 350° C. and pressures in the range of from about 10 to about 300 atmospheres. In the preferred embodiment of the invention the pressures which are employed will be the autogeneous pressures resulting from the presence of carbon monoxide and hydrogen as well as the olefins, if in gaseous form in the reaction mixture, although it is also contemplated within the scope of this invention that the pressures resulting from the use of carbon monoxide and hydrogen will comprise only a partial operating pressure, the remainder being provided for by the introduction of a substantially inert gas such as nitrogen, helium, argon, etc., into the reaction vessel. Other reaction conditions which are present during the synthesis of the tertiary amines will include mole ratios of the various components. For example, the carbon monoxide which is employed in the reaction mixture will be present in a mole ratio in the range of from about 1:1 to about 100:1 moles of carbon monoxide/mole of olefinic compound; 1:1 to about 3:1 moles of olefinic compound/mole of nitrogen-containing compound, and 0.5:1 to about 3:1 moles of hydrogen/mole of carbon monoxide.

Examples of olefinic compounds which may be employed as one of the components of the reaction mixture will include open chain compounds containing from 2 to about 30 carbon atoms such as ethylene, propylene, 1-butene, 2-butene, 1-pentene, 2-pentene, 1-hexene, 2-hexene, 3-hexene, 1-heptene, 2-heptene, 3-heptene, 1-octene, 2-octene, 3-octene, 4-octene, the isomeric straight chain nonenes, decenes, undecenes, dodecenes, tridecenes, tetradecenes, pentadecenes, hexadecenes, heptadecenes, octadecenes, nonadecenes, eicosenes, henicosenes, docosenes, tricosenes, tetracosenes, pentacosenes, hexacosenes, heptacosenes, octacosenes, nonacosenes, triacontenes, etc., as well as branched chain isomers thereof, cycloalkenes such as cyclopentene, cyclohexene, cycloheptene, cyclooctene, etc., diolefines such as 1,3-butadiene, 1,3-pentadiene, 1,3-hexadiene, 2,4-hexadiene, 1,3-heptadiene, 2,4-heptadiene, the isomeric octadienes, nonadienes, decadienes, undecadienes, dodecadienes, etc.

The aforesaid olefinic compounds are reacted with a nitrogen-containing compound having the formula:

in which the R's are independently selected from the group consisting of hydrogen, alkyl, aryl, cycloalkyl, aralkyl, and alkaryl radicals. Specific examples of this nitrogen-containing compound which constitutes a second component of the reaction mixture will include ammonia, primary amines such as methylamine, ethylamine, n-propylamine, isopropylamine, n-butylamine, t-butylamine, N-pentylamine, sec-pentylamine, the isomeric hexylamines, heptylamines, octylamines, nonylamines, decylamines, undecylamines, dodecylamines, tridecylamines, tetradecylamines, etc., aniline, o-toluidine, m-toluidine, p-toluidine, o-xylidine, m-xylidine, p-xylidine, 2-ethylaniline, 3-ethylaniline, 4-ethylaniline, 2-propylaniline, 3-propylaniline, 4-propylaniline, cyclopentylamine, cyclohexylamine, cycloheptylamine, cyclooctylamine, etc., secondary amines such as dimethylamine, diethylamine, di-n-propylamine, diisopropylamine, di-n-butylamine, di-t-butylamine, di-n-pentylamine, di-sec-pentylamine, the isomeric dihexylamines, diheptylamines dioctylamines, dinonylamines, didecylamines, diundecylamines, didodecylamines, ditridecylamines, ditetradecylamines, etc., dianiline, di-o-toluidine, di-m-toluidine, di-p-toluidine, di-o-xylidine, di-m-xylidine, di-p-xylidine, di-2-ethylaniline, di-3-ethylaniline, di-4-ethylaniline, di-2-propylaniline, di-3-propylaniline, di-4-propylaniline, dicyclopentylamine, dicyclohexylamine, dicycloheptylamine, dicyclooctylamine, etc. It is to be understood that the aforementioned olefinic compounds and nitrogen-containing compounds are only representative of the class of compounds which may be employed as reactants, and that the present invention is not necessarily limited thereto.

The reaction between the aforementioned olefinic compounds, nitrogen-containing compounds, carbon monoxide and hydrogen is effected in the presence of certain catalytic compositions of matter, said compositions comprising rhodium- or ruthenium-containing compounds. In the preferred embodiment of the invention, the ruthenium- or rhodium-containing compounds will comprise the metals or the nitrates, halides, halocarbonyls or carbonyl complexes. Specific examples of these compounds which are employed will include rhodium, rhodium nitrate, rhodium chloride, rhodium bromide, rhodium iodide, rhodium fluoride, chlorodicarbonylrhodium dimer, rhodium carbonyl, chlorobis(ethylene)rhodium dimer, ruthenium, ruthenium nitrate, ruthenium chloride, ruthenium bromide, ruthenium iodide, ruthenium fluoride, dichlorotricarbonylruthenium dimer, ruthenium carbonyl, etc.

The process of the present invention may be effected in any suitable manner and may comprise either a batch or continuous type of operation. When a batch type operation is used, a quantity of the olefin and the nitrogen-containing compound, if in solid or liquid form, is placed in an appropriate pressure resistant apparatus such as an autoclave of the rotating or mixing type which contains a predetermined amount of the rhodium- or ruthenium-containing compound. The autoclave is then sealed and carbon monoxide and hydrogen are charged thereto until the desired operating pressure is reached. Alternatively, as hereinbefore discussed, if higher pressure are to be employed, a portion of the pressure may be afforded by the introduction of a substantially inert gas into the reaction mixture along with the carbon monoxide and hydrogen. After the proper operating pressure has been attained, the autoclave is then heated to the desired operating temperature which may range from about 50° to about 350° C. or more and the apparatus maintained thereat for a predetermined residence time which may range from about 0.5 up to about 10 hours or more in duration. Upon completion of the residence time, heating is discontinued and the autoclave and contents thereof are allowed to return to room temperature. Upon reaching room temperature the excess pressure is discharged, the autoclave is opened and the reaction mixture is recovered therefrom. After separation from the catalyst, the reaction mixture may then be subjected to conventional means of separation whereby the desired tertiary amine is separated from unreacted stating materials and/or unwanted side reaction products which may have been formed and recovered.

It is also contemplated within the scope of this invention that the synthesis of tertiary amines may be accomplished by utilizing a continuous method of operation.

When utilizing this type of operation, the olefinic compound and the nitrogen-containing compound are continuously charged to a reaction zone which is maintained at the proper operating conditions of temperature and pressure, said reaction zone containing a catalyst of the type hereinbefore set forth. In addition, carbon monoxide and hydrogen are also continuously charged to the reaction zone through separate lines or, if so desired, they may be admixed prior to entry into said zone and the resulting mixture charged thereto in a single stream. Upon completion of the desired residence time in the reaction zone, the reactor effluent is continuously withdrawn and subjected to conventional means of separation such as fractional distillation whereby the desired tertiary amine is separated from unreacted starting materials and recovered, while the aforesaid unreacted starting materials may be recycled to the reaction zone to form a portion of the feed stock.

Some specific examples of the types of tertiary amines which may be prepared according to the process of this invention will include propyldimethylamine, butyldimethylamine, pentyldimethylamine, hexyldimethylamine, heptyldimethylamine, octyldimethylamine, decyldimethylamine, dodecyldimethylamine, tetradecyldimethylamine, pentadecyldimethylamine, octadecyldimethylamine, eicosyldimethylamine, docosyldimethylamine, propyldiethylamine, octyldiethylamine, nonyldiethylamine, undecyldiethylamine, pentadecyldiethylamine, octadecyldiethylamine, tripropylamine, butyldipropylamine, hexyldipropylamine, nonyldipropylamine, decyldipropylamine, tridecyldipropylamine, heptadecyldipropylamine, eicosyldipropylamine, tributylamine, pentyldibutylamine, octyldibutylamine, decyldibutylamine, undecyldibutylamine, tetradecyldibutylamine, nonadecyldibutylamine, phenyldiethylamine, phenyldipropylamine, phenyldioctylamine, phenyldidecylamine, phenylditetradecylamine, phenyldioctadecylamine, phenyldidocosylamine, cyclohexyldipropylamine, cyclohexyldihexylamine, cyclohexyldidecylamine, cyclohexyldidodecylamine, propyldiphenylamine, hexyldiphenylamine, octyldiphenylamine, undecyldiphenylamine, tetradecyldiphenylamine, propyldicyclohexylamine, hexyldicyclohexylamine, octyldicyclohexylamine, undecyldicyclohexylamine, tetradecyldicyclohexylamine, octyldi(p-tolyl)amine, decyldi(p-tolyl)amine, etc. It is to be understood that the aforementioned tertiary amines are only representative of the class of compounds which may be prepared according to the process described herein, and that the present invention is not necessarily limited thereto.

The following examples are given to illustrate the process of the present invention. However, it is to be understood that these examples are given merely for purposes of illustration and that the present invention is not necessarily limited thereto.

EXAMPLE I

In the example, 0.1 grams of a catalyst comprising rhodium chloride was placed in the glass liner of a rotating autoclave. In addition, 11.0 grams of dimethylamine and 37.6 grams of undecene were also placed in the autoclave. The autoclave was sealed and a 1:1 mixture of carbon monoxide and hydrogen was charged to the autoclave until 150 atmospheres of the blend gas had been charged. The autoclave was then heated to a temperature of 153° C. and maintained thereat for a period of 3 hours. During this period the pressure in the autoclave dropped from 190 atmospheres to 163 atmospheres. At the end of the 3 hour period heating was discontinued and the autoclave was allowed to return to room temperature. Upon reaching room temperature the excess pressure was discharged and the reaction mixture was recovered therefrom. Analysis of the product by means of gas liquid chromatography and elementary analysis showed that there had been a 100% conversion of the undecene with a 96% selectivity to dodecyldimethylamine.

EXAMPLE II

In a manner similar to that set forth in Example I above, 0.029 grams of a catalyst comprising chlorodicarbonylrhodium dimer, 11.0 grams of dimethylamine and 36.9 grams of undecene were placed in the glass liner of a rotating autoclave which was sealed and a blend gas of a 1:1 mole ratio of carbon monoxide and hydrogen was placed thereto. The autoclave was then heated to a temperature of 156° C. and maintained thereat for a period of 3 hours, the initial pressure of 186 atmospheres dropping to 165 atmospheres during the reaction period. Upon completion of the 3 hour period, heating was discontinued and the autoclave was allowed to return to room temperature. The excess pressure was discharged, the autoclave was opened and the reaction mixture was recovered therefrom. Analysis of the mixture by means of gas liquid chromatography and elementary analysis determined that there had been a 100% conversion of the olefin with an 80% selectivity to dodecyldimethylamine.

EXAMPLE III

In this example, 0.0453 grams of a catalyst comprising chlorobis(ethylene)rhodium dimer, 37.8 grams of undecene and 11.0 grams of dimethylamine were treated in a manner similar to that set forth in the above examples. The autoclave, after being pressured with a 1:1 mole ratio of carbon monoxide and hydrogen, was heated to a temperature of 151° C. and maintained thereat for a period of 3 hours. During this time, the pressure dropped from 169 atmospheres to 160 atmospheres. At the end of the reaction time, heating was discontinued and after the autoclave had returned to room temperature the excess pressure was discharged. The autoclave was opened and the reaction mixture which was recovered therefrom was subjected to gas liquid chromatographic analysis and elementary analysis. These analyses determined that there had been a 100% conversion of the undecene with an 85% selectivity to dodecyldimethylamine.

EXAMPLE IV

To illustrate the operability of other nitrogen-containing compounds, 0.036 grams of a chlorodicarbonylrhodium dimer were placed in the glass liner of a rocking autoclave along with 49.85 grams of undecene. The autoclave was sealed and ammonia was charged thereto in an amount sufficient to afford a 1.1:1 mole ratio of undecene to ammonia. In addition, a blend gas consisting of equimolar amounts of carbon monoxide and hydrogen was charged to the autoclave until the initial operating pressure was 175 atmospheres. The autoclave was then heated to a temperature of 150° C. and maintained thereat for a period of 3 hours during which time a pressure drop to 142 atmospheres occurred. At the end of the 3 hour period, heating was discontinued and the autoclave was allowed to return to room temperature. The excess pressure was discharged, the autoclave was opened and the reaction mixture recovered therefrom. Gas liquid chromatographic analysis and elementary analysis of the mixture disclosed the fact that there had been a 100% conversion of the olefin with an 88% selectivity to tridecylamine.

EXAMPLE V

In this example, 0.03 grams of rhodium chloride along with 15.23 grams of aniline and 50.05 grams of undecene were placed in the glass liner of a rocking autoclave which was then sealed. The autoclave was pressured with a 1:1 equimolar mixture of carbon monoxide and hydrogen following which the autoclave was heated to a temperature of 150° C. The autoclave was maintained at this temperature for a period of 3 hours during which time a pressure drop of from 195 atmospheres to 150 atmospheres took place. At the end of the 3 hour period, heating was discontinued and after reaching room temperature the excess pressure was discharged. After opening the autoclave and recovering the reaction mixture therefrom, the mixture was subjected to gas liquid chromatographic analysis and elementary analysis. These analyses disclosed that there had been a 97.6% conversion of the undecene with a 100% selectivity to N,N-di(dodecyl)aniline.

When the above experiment was repeated using 54.18 grams of diphenylamine in place of aniline, the analysis of the reaction product by means of gas liquid chromatography and elementary analysis disclosed a 70.6% conversion of the undecene with a 23% selectivity to dodecyldiphenylamine.

EXAMPLE VI

In a manner similar to that set forth in the above examples, 0.103 grams of rhodium chloride, 11 grams of dimethylamine and 34.40 grams of n-heptene were placed in an autoclave which was thereafter sealed. A blend gas comprising 50 atmospheres of carbon monoxide and 100 atmospheres of hydrogen was charged to the autoclave which was thereafter heated to a temperature of 151° C. The autoclave was maintained at this temperature for a period of 3 hours during which time a pressure drop of from 98 atmospheres to 75 atmospheres was observed. At the end of the 3 hour period heating was again discontinued and after reaching room temperature, the excess pressure was discharged. The autoclave was then opened and after recovering the reaction mixture therefrom, the mixture was analyzed by means of gas liquid chromatography and elementary analysis. It was found that there had been an approximate 100% conversion of the undecene with a 90% selectivity to octyldimethylamine.

EXAMPLE VII

In this example, 0.117 grams of rhodium chloride, 14 grams of dimethylamine and 80.13 grams of docosene were placed in an autoclave which was sealed and pressured with 150 atmospheres of a blend gas consisting of equimolar amounts of hydrogen and carbon monoxide. The autoclave was then heated to a temperature of 153° C. and maintained thereat for a period of 3 hours. At the end of this time the apparatus and contents thereof were treated in a manner similar to that set forth in the above examples. Gas liquid chromatographic analysis and elementary analysis disclosed that there had been a 100% conversion of the docosene with a 90% selectivity to tricosyldimethylamine.

EXAMPLE VIII

In a manner similar to that set forth in the above examples, a mixture consisting of a catalyst comprising ruthenium carbonyl, butylamine and tetradecene may be placed in an autoclave which is sealed and a blend gas consisting of equimolar proportions of carbon monoxide and hydrogen may be charged thereto. The autoclave may be heated to a temperature of about 150° C. and maintained at this temperature for a period of 4 hours at the end of which time heating may be discontinued and the autoclave allowed to return to room temperature. After returning to room temperature, the excess pressure may be discharged and the autoclave opened. The reaction mixture may then be subjected to gas liquid chromatographic analysis and elementary analysis to determine the presence of the desired tertiary amine, namely, di(pentadecyl)butylamine.

I claim as my invention:

1. A process for the preparation of tertiary amines which comprises reacting an olefinic compound, carbon monoxide, hydrogen and a nitrogen-containing compound having the formula:

in which the R's are independently selected from the group consisting of hydrogen, alkyl, aryl, cycloalkyl, aralykyl and alkaryl radicals in the presence of a rhodium catalyst selected from the group consisting of rhodium metal, nitrate, halides, chlorodicarbonylrhodium dimer and chlorobis(ethylene)rhodium dimer, and recovering the resultant tertiary amine.

2. The process as set forth in claim 1 in which said reaction is effected at a temperature in the range of from about 50° to about 350° C. and a pressure in the range of from about 10 to about 300 atmospheres.

3. The process as set forth in claim 1 in which said catalyst is rhodium chloride.

4. The process as set forth in claim 1 in which said catalyst is chlorodicarbonylrhodium dimer.

5. The process as set forth in claim 1 in which said catalyst is chlorobis(ethylene)rhodium dimer.

6. The process as set forth in claim 1 in which said nitrogen-containing compound is dimethylamine, said olefin is undecene and said tertiary amine is dodecyldimethylamine.

7. The process as set forth in claim 1 in which said nitrogen-containing compound is dimethylamine, said olefin is heptene and said tertiary amine is octyldimethylamine.

8. The process as set forth in claim 1 in which said nitrogen-containing compound is aniline, said olefin is octene, and said tertiary amine is dinonylaniline.

9. The process as set forth in claim 1 in which said nitrogen-containing compound is ammonia, said olefin is pentene, and said tertiary amine is trihexylamine.

10. The process as set forth in claim 1 in which said nitrogen-containing compound is butylamine, said olefin is tetradecene, and said tertiary amine is di(pentadecyl)butylamine.

* * * * *